US006789272B2

(12) United States Patent
Thorson

(10) Patent No.: US 6,789,272 B2
(45) Date of Patent: Sep. 14, 2004

(54) EYE GLASS PERSPIRATION GUARD

(76) Inventor: Bjorne Paul Thorson, 3250 County Rd. 67, Penrose, CO (US) 81240

( * ) Notice: Subject to any disclaimer, the term of this patent is extended or adjusted under 35 U.S.C. 154(b) by 0 days.

(21) Appl. No.: 10/314,144

(22) Filed: Dec. 9, 2002

(65) Prior Publication Data

US 2004/0107483 A1 Jun. 10, 2004

(51) Int. Cl.⁷ .............................. A61F 9/02; G02C 11/08
(52) U.S. Cl. ..................... 2/426; 2/13; 351/62; 351/123
(58) Field of Search ............................. 2/13, 181, 426, 2/431, 452, 453; 351/62, 123, 156, 157, 155

(56) References Cited

U.S. PATENT DOCUMENTS

| | | | |
|---|---|---|---|
| 2,393,837 A | * | 1/1946 | Swanson ..................... 351/62 |
| 3,133,982 A | * | 5/1964 | Janz ............................ 351/62 |
| 3,578,736 A | | 5/1971 | Dootson |
| 3,874,776 A | * | 4/1975 | Seron ......................... 351/123 |
| 4,393,519 A | | 7/1983 | Nicastro |
| 4,549,793 A | * | 10/1985 | Yoon ........................... 351/156 |
| 4,616,367 A | * | 10/1986 | Jean et al. ..................... 2/452 |
| 4,626,247 A | | 12/1986 | Frankel |
| 4,856,116 A | | 8/1989 | Sullivan |
| 5,009,496 A | * | 4/1991 | Holtan et al. ............... 351/156 |
| 5,032,018 A | * | 7/1991 | McCulley et al. ........... 351/156 |
| 5,056,163 A | * | 10/1991 | Chou ............................ 2/453 |
| 5,146,630 A | | 9/1992 | Richard |
| 5,384,605 A | * | 1/1995 | Escobosa .................... 351/123 |
| 5,428,844 A | | 7/1995 | Dougherty |
| 5,822,799 A | | 10/1998 | Kepple |
| 5,887,284 A | | 3/1999 | Simmons |
| 6,138,280 A | | 10/2000 | Bae |
| 6,282,727 B1 | * | 9/2001 | Lindahl ......................... 2/428 |
| 6,450,640 B1 | * | 9/2002 | Van Rysselberghe ....... 351/123 |
| 2002/0100107 A1 | | 8/2002 | Shin |
| 2003/0041365 A1 | * | 3/2003 | Sanchez ..................... 2/181.6 |

OTHER PUBLICATIONS

Airarc.com website, pp. 5–6, including Browmount and DryBrow® Sweatbands.
Emergency Response—Outdoor Protection Product Brochure, p. 2, including MiraCool™ Terry Coolers and Terri–Band™ Sweatband.
VillageHatShop.com website, p. 4, including Cap–Ban–Nu Disposable Sweatband.
Omark Safety Online website, 6 pages.
The present inventor has described having seen in private use a foam rubber strip with holes in each end of the strip for inserting the arms of eyeglasses, developed by his father, Bennie Thorson, with the present inventor also contributing to development. This could be deemed to be prior art but we assert it is not.

* cited by examiner

Primary Examiner—Rodney M. Lindsey
(74) Attorney, Agent, or Firm—Holme Roberts & Owen LLP; Susan D. Campbell, Esq.

(57) ABSTRACT

The "Eye Glass Perspiration Guard" which is fixed by means of rubber "O" rings to the eye glass arms enables individuals the use of a "sweat band" type device without having to be secured around the head. With the close proximity of the "Eye Glass Perspiration Guard" to the eye glasses, dust and dirt can also be reduced and or eliminated from entrance from the top of the eye glasses. Hats and or hard hats will not be interfered with as with head constraint "sweat bands".

8 Claims, 2 Drawing Sheets

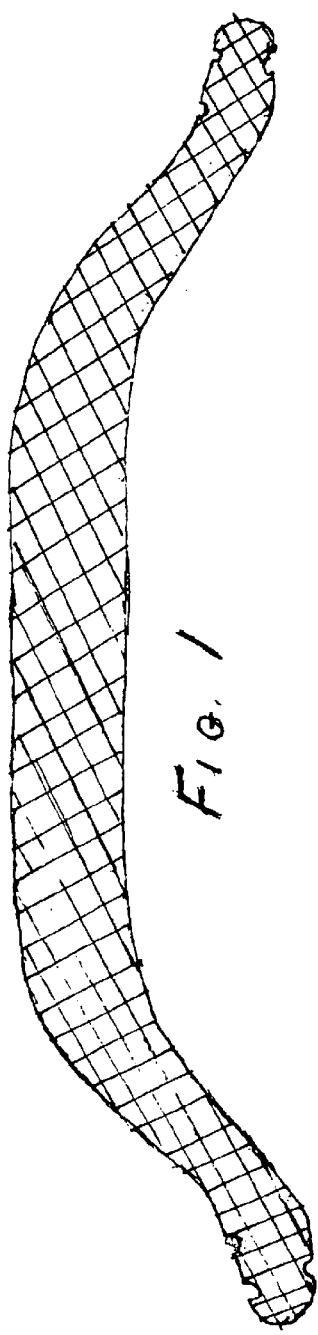
FIG. 1
FIG. 2
Legend
Absorbent Foam
Flexible Plastic

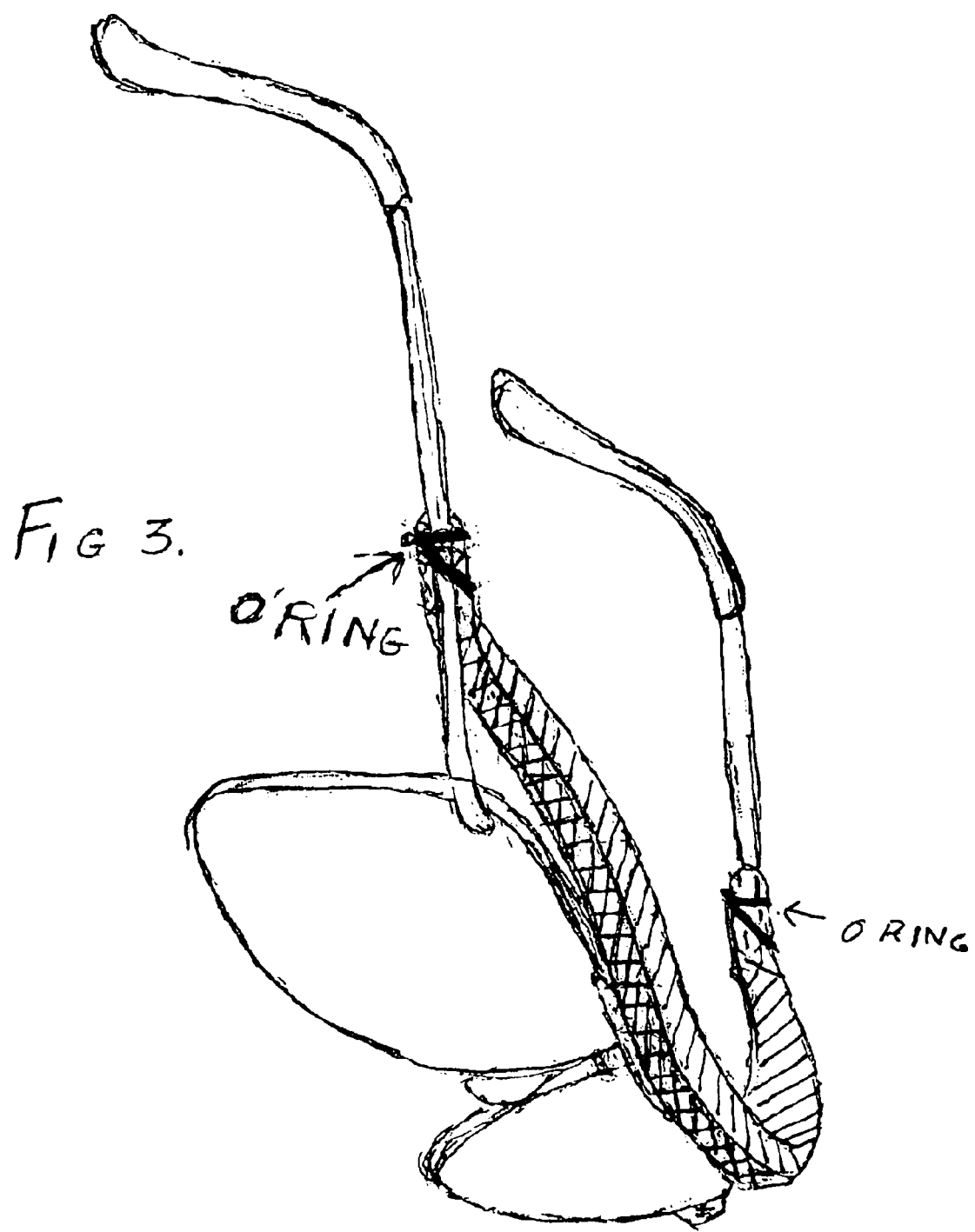

EYE GLASS PERSPIRATION GUARD

CROSS REFERENCE TO RELATED APPLICATIONS

To the best of my knowledge, there are no prior filed copending nonprovisional applications in the United States of America.

I Bjorne Paul Thorson have not received any form of Federal sponsorship, nor Federal sponsored R&D.

SEQUENCE LISTING. N/A

BACKGROUND OF THE INVENTION

The use of the "Eye Glass Perspiration Guard" is targeted for the construction work place, but not limited to these areas. Welders, maintenance personnel, sportsman and or any other people who wear eye glasses and or safety glasses can use this invention to limit the amount of perspiration interference to their glasses or eyes. In addition, "Sweat Bands" which may be similar but are attached to the head by means of elastic bands or similar constraints can interfere with the use of "Hard Hats". The "Eye Glass Perspiration Guard" being attached to eye glasses does not interfere with "Hard Hats", therefore is unique.

SUMMARY OF THE INVENTION

With the "Eye Glass Perspiration Guard" attached to a pair of eye glasses or safety glasses by use of the (2) "O" rings, the absorbent foam rubber comes in contact with the forehead and soaks up the perspiration before the perspiration can fall onto the eye glasses or into the eyes, therefore not having to clean eye glasses as often.

DESCRIPTION OF DRAWINGS

FIG. 1 This is the front view of the "Eye Glass Perspiration Guard.

FIG. 2 This is the top view of the "Eye Glass Perspiration Guard.

FIG. 3 This is a view with the "Eye Glass Perspiration Guard" attached to a pair of eye glasses.

DETAILED DESCRIPTION

A device which is comprised of (4) parts. The first is a piece of foam rubber with the characteristics for the absorption of water. The second is a piece of thin plastic cut to the same dimension of the foam rubber to give rigidity and to incorporate (2) rubber "O" rings for the attachment to the upper part of the eye glass frame.

The first piece is stamp cut from a ¼" to ½' thick sheet of foam rubber. The second piece is stamp cut from a 1/64" thick sheet of plastic. The (2) pieces are glued together with cyanoacrylate to form a semi rigid component which then can be attached with "O" rings on each end for attachment to eye glasses and or safety glasses.

I claim:

1. An apparatus for use with eyeglasses, said eyeglasses including a frame supporting two lenses, a nose piece, and two arms, comprising:

a first piece formed of an elongated sheet of liquid-absorbent foam rubber;

a second piece formed from an elongated plastic sheet of about the same size and shape as the first piece, the second piece being glued to the first piece, and the second piece and the first piece together forming a component having a center portion, a first end and a second end, each of the first end and the second end being attachable to the arms of the eyeglasses, and the center portion of said component positioned proximate the top of said lenses, and oriented with the first piece at least in partial contact with the forehead of the wearer of the eyeglasses wherein said first piece is of a length approximately the width of the frame of the eyeglasses.

2. The apparatus of claim 1, wherein said component is attachable to said arms and positioned proximate the top of said lenses, in close contact with the wearer's forehead, so providing at least a partial barrier to dust and dirt that might blow into the wearer's eyes over the top of the eyeglasses.

3. The apparatus of claim 1, wherein said component is attachable to a pair of safety glasses of the wearer instead of eyeglasses.

4. The apparatus of claim 1, wherein said component is attachable to the arms of said eyeglasses with O-rings wrapped around each of said first end and second end and each of the arms of the eyeglasses, the O-rings positioned at indentations formed in each of said first end and second end.

5. The apparatus of claim 1, wherein said component is attachable to each of said arms in a location causing said first piece to snugly contact the forehead of said wearer, in a position wherein perspiration forming on the wearer's forehead is absorbed by said first piece and impeded from flowing into said wearer's eyes.

6. The apparatus of claim 1, wherein said second piece is formed from a piece of plastic of about 1/64 of an inch thick.

7. The apparatus of claim 1, wherein said first piece and also extending along at least a portion of each of said arms of said eyeglasses.

8. The apparatus of claim 1, wherein said first piece is a sheet of foam rubber having a thickness of about ¼ to about ½ inch.

* * * * *